(12) United States Patent
Ahmed et al.

(10) Patent No.: US 8,541,638 B2
(45) Date of Patent: *Sep. 24, 2013

(54) PROCESS TO REMOVE DISSOLVED ALCL$_3$ FROM IONIC LIQUID

(75) Inventors: Moinuddin Ahmed, Hercules, CA (US); Huping Luo, Richmond, CA (US); Krishniah Parimi, Alamo, CA (US); Bong-Kyu Chang, Novato, CA (US); Sara Lindsay, Houston, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 1337 days.

This patent is subject to a terminal disclaimer.

(21) Appl. No.: 12/324,570

(22) Filed: Nov. 26, 2008

(65) Prior Publication Data

US 2010/0130799 A1   May 27, 2010

(51) Int. Cl.
 *C07C 2/08* (2006.01)
 *B01J 20/34* (2006.01)
 *B01J 27/132* (2006.01)
 *B01J 27/135* (2006.01)
 *B01J 27/138* (2006.01)
 *B01J 27/06* (2006.01)
 *B01J 31/00* (2006.01)
 *C07C 45/46* (2006.01)

(52) U.S. Cl.
 USPC ............. 585/311; 502/21; 502/150; 502/155; 502/167; 502/224; 502/226; 502/227; 502/228; 585/438

(58) Field of Classification Search
 None
 See application file for complete search history.

(56) References Cited

U.S. PATENT DOCUMENTS

| | | | |
|---|---|---|---|
| 5,300,685 A | 4/1994 | Scates et al. | |
| 5,712,214 A | 1/1998 | Huang et al. | |
| 8,012,899 B2 * | 9/2011 | Hommeltoft | 502/24 |
| 2006/0131209 A1 | 6/2006 | Timken et al. | |
| 2006/0135839 A1 | 6/2006 | Elomari et al. | |
| 2007/0142211 A1 * | 6/2007 | Elomari et al. | 502/29 |
| 2007/0142676 A1 * | 6/2007 | Elomari et al. | 568/354 |
| 2009/0163349 A1 * | 6/2009 | Elomari et al. | 502/26 |

OTHER PUBLICATIONS

PCT/US2009/065744 Search Report and Written Opinion, International Filing Date Nov. 24, 2009, 10 pages.
U.S. Appl. No. 12/003,578, filed Dec. 28, 2007, entitled "Process for Ionic Liquid Catalyst Regeneration", Bong-Kyu Chang, et al.
PCT/US2009/065744. PCT International Preliminary Report on Patentability, mailed Jun. 9, 2011.

* cited by examiner

*Primary Examiner* — Yun Qian
(74) *Attorney, Agent, or Firm* — Merchant & Gould

(57) ABSTRACT

Disclosed herein are processes in which precipitation permits removal of metal halides (e.g. AlCl$_3$) from ionic liquids. After precipitation, the precipitated metal halides can be physically separated from the bulk ionic liquid. More effective precipitation can be achieved through cooling or the combination of cooling and the provision of metal halide seed crystals. The ionic liquids can be regenerated ionic liquid catalysts, which contain excess metal halides after regeneration. Upon removal of the excess metal halides, they can be reused in processes using ionic liquid catalysts, such as alkylation processes.

10 Claims, 2 Drawing Sheets

PROCESS TO REMOVE DISSOLVED ALCL₃ FROM IONIC LIQUID

FIELD OF ART

The present disclosure relates to a process for removing metal halides from an ionic liquid. In particular, the process involves precipitating metal halides out of a mixture comprising the ionic liquid and metal halides. More particularly, the present disclosure relates to removing metal halides (e.g. $AlCl_3$) from a regenerated ionic liquid catalyst involving precipitating metal halides out of a mixture comprising the regenerated ionic liquid catalyst and metal halides.

BACKGROUND

An alkylation process, which is disclosed in U.S. Patent Application Publication 2006/0131209 ("the '209 publication"), involves contacting isoparaffins, preferably isopentane, with olefins, preferably ethylene, in the presence of an ionic liquid catalyst to produce gasoline blending components. The contents of the '209 publication are incorporated by reference herein in its entirety.

An ionic liquid catalyst distinguishes this novel alkylation process from conventional processes that convert light paraffins and light olefins to more lucrative products such as the alkylation of isoparaffins with olefins and the polymerization of olefins. For example, two of the more extensively used processes to alkylate isobutane with $C_3$-$C_5$ olefins to make gasoline cuts with high octane numbers use sulfuric acid ($H_2SO_4$) and hydrofluoric acid (HF) catalysts.

Ionic liquid catalysts specifically useful in the alkylation process described in the '209 publication are disclosed in U.S. Patent Application Publication 2006/0135839 ("the '839 publication"), which is also incorporated by reference in its entirety herein. Such catalysts include a chloroaluminate ionic liquid catalyst comprising a hydrocarbyl substituted pyridinium halide and aluminum trichloride or a hydrocarbyl substituted imidazolium halide and aluminum trichloride. Such catalysts further include chloroaluminate ionic liquid catalysts comprising an alkyl substituted pyridinium halide and aluminum trichloride or an alkyl substituted imidazolium halide and aluminum trichloride. Preferred chloroaluminate ionic liquid catalysts include 1-butyl-4-methyl-pyridinium chloroaluminate (BMP), 1-butyl-pyridinium chloroaluminate (BP), 1-butyl-3-methyl-imidazolium chloroaluminate (BMIM) and 1-H-pyridinium chloroaluminate (HP).

However, ionic liquid catalysts have unique properties making it necessary to further develop and modify the ionic liquid catalyzed alkylation process in order to achieve superior gasoline blending component products, improved process operability and reliability, reduced operating costs, etc. For example, as a result of use, ionic liquid catalysts become deactivated, i.e. lose activity, and may eventually need to be replaced.

Alkylation processes utilizing an ionic liquid catalyst form by-products known as conjunct polymers. These conjunct polymers can deactivate the ionic liquid catalyst by forming complexes with the ionic liquid catalyst. Conjunct polymers are highly unsaturated molecules and may complex the Lewis acid portion of the ionic liquid catalyst via their double bonds network system. As the aluminum trichloride becomes complexed with conjunct polymers, the activity of the ionic liquid becomes impaired or at least compromised. Conjunct polymers may also become chlorinated and through their chloro groups may interact with aluminum trichloride and therefore reduce the overall activity of the catalyst or lessen its effectiveness as a catalyst for the intended purpose such as alkylation. Deactivation of the ionic liquid catalyst by conjunct polymers is not only problematic for the alkylation chemistry, but also weighs in heavily on the economics of using ionic liquids because they are expensive catalytic systems and their frequent replacement will be costly. Therefore, commercial exploitation of ionic liquid catalysts during alkylation is impossible unless they are efficiently regenerated and recycled.

U.S. patent application Ser. No. 12/003,578 ("the '578 application) is directed to a process for regenerating an ionic liquid catalyst which has been deactivated by conjunct polymers. The process comprises the steps of (a) providing an ionic liquid catalyst, wherein at least a portion of the ionic liquid catalyst is bound to conjunct polymers; (b) reacting the ionic liquid catalyst with aluminum metal to free the conjunct polymers from the ionic liquid catalyst in a stirred reactor or a fixed bed reactor; and (c) separating the freed conjunct polymers from the catalyst phase by solvent extraction in a stirred or packed extraction column. The contents of the '578 application are incorporated by reference herein in their entirety.

In order to provide regenerated ionic liquid catalyst, in the process of the '578 application, spent ionic liquid catalyst reacts with aluminum metal. If the spent ionic liquid catalyst is a chloroaluminate ionic liquid catalyst, such as catalysts disclosed in the '839 publication, it produces aluminum trichloride ($AlCl_3$) as a byproduct. The $AlCl_3$ byproduct can remain dissolved in the regenerated catalyst. Accordingly, it is necessary to separate the regenerated catalyst and the $AlCl_3$ byproduct so that the regenerated catalyst can be recycled to the alkylation step.

Therefore, there is a need for an effective and efficient process for removing metal halides from an ionic liquid catalyst, and, in particular, a regenerated ionic liquid catalyst. In general, the process should be simple and efficient enough to be used to separate any metal halide from an ionic liquid.

SUMMARY

A process for removing metal halides from an ionic liquid is described herein. In one embodiment, the process for removing metal halides from an ionic liquid comprises causing the metal halides to precipitate out of the ionic liquid. Enhanced precipitation can be caused by cooling. Cooling can also cause precipitation, which can provide metal halide seed crystals.

In another embodiment, a process for removing metal halides from an ionic liquid comprises: a) feeding the ionic liquid comprising metal halides to a vessel and providing metal halide seed crystals to provide a mixture comprising ionic liquid, metal halides, and metal halide seed crystals; b) cooling the mixture in the vessel to provide precipitated metal halides; and c) removing the precipitated metal halides from the vessel.

The ionic liquid may be an ionic liquid catalyst, which, after use, may be regenerated in a manner that produces excess metal halides (e.g. $AlCl_3$) in the regenerated ionic liquid catalyst. Therefore, a process for regenerating an ionic liquid catalyst is also disclosed herein. The process includes: a) reacting an ionic liquid catalyst with aluminum to provide a regenerated ionic liquid catalyst containing excess $AlCl_3$; b) precipitating the excess $AlCl_3$ from the regenerated ionic liquid catalyst to provide precipitated excess $AlCl_3$; and c) removing the precipitated excess $AlCl_3$ from the regenerated ionic liquid catalyst.

The ionic liquid catalyst and regenerated ionic liquid catalyst can be utilized in an alkylation reaction. Therefore, an alkylation process is further disclosed herein. The alkylation process includes: a) conducting an alkylation reaction with an ionic liquid catalyst to provide a product and a spent ionic liquid catalyst; b) reacting the spent ionic liquid catalyst with aluminum to provide a regenerated ionic liquid catalyst and excess $AlCl_3$; c) precipitating the excess $AlCl_3$ from the regenerated ionic liquid catalyst to provide precipitated excess $AlCl_3$; d) removing the precipitated excess $AlCl_3$ from the regenerated ionic liquid catalyst; and e) recycling the regenerated ionic liquid catalyst to reaction step a).

DETAILED DESCRIPTION

Figure 1:
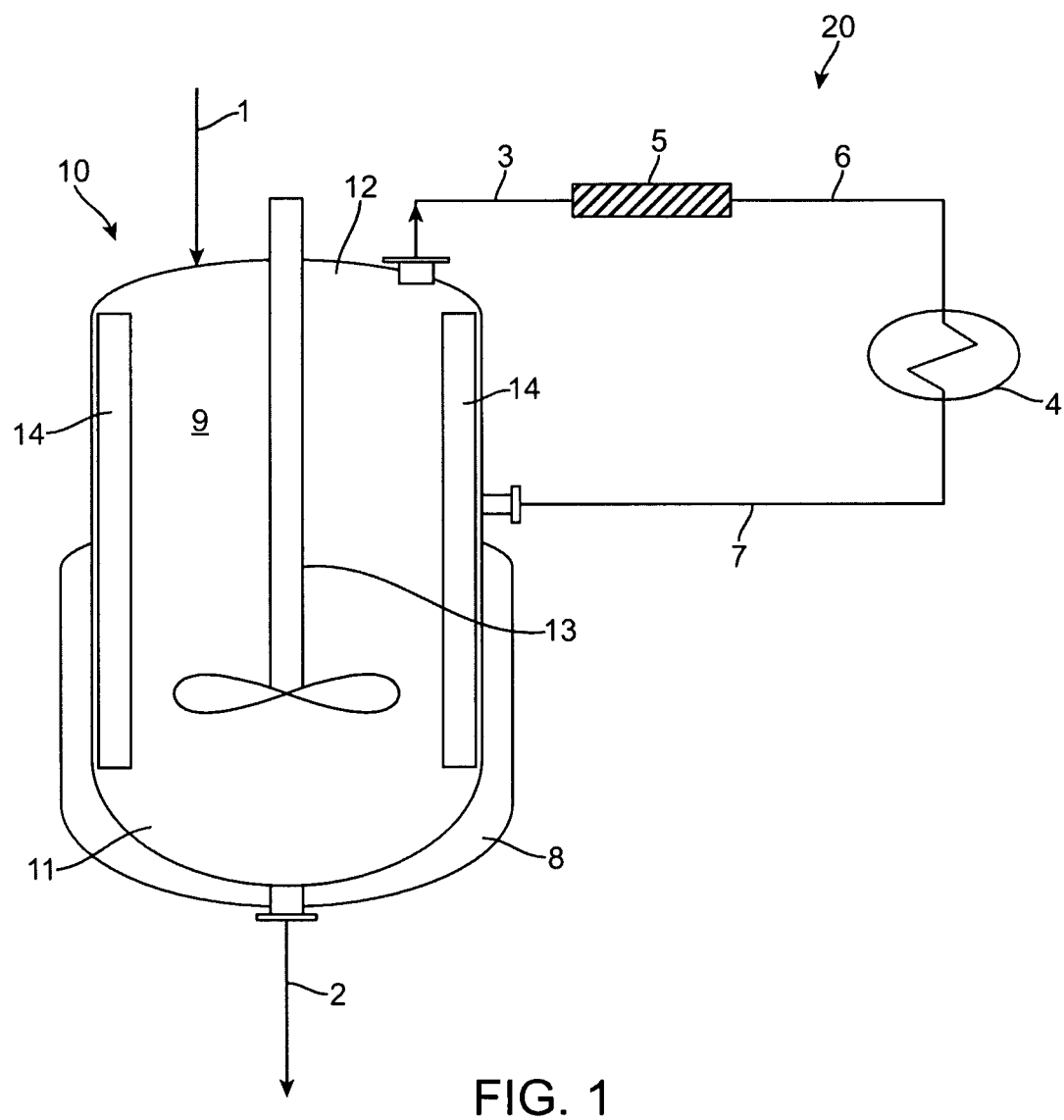
FIG. 1 is a schematic illustration of an embodiment of the process whereby metal halides are removed from an ionic liquid in a crystallization vessel.

Process for Removing Metal Halides from Ionic Liquid

In one aspect, the present process is directed to removing metal halides from an ionic liquid by precipitation. Accordingly, the present process involves causing the metal halides to precipitate out of the ionic liquid.

In one embodiment, the process involves cooling a mixture comprising the metal halides and ionic liquid to precipitate the metal halides out of the ionic liquid. Cooling facilitates precipitation of the metal halides from the mixture. Upon cooling, the metal halides generally first form metal halide seed crystals, which are extremely small, solid particles of the metal halide. The reduced temperature then facilitates precipitation of additional metal halide onto the metal halide seed crystals, causing the metal halide seed crystals to grow into larger, solid particles of precipitated metal halides. Accordingly, the process can further involve cooling a mixture comprising metal halides and ionic liquid containing metal halide seed crystals.

It has been discovered that cooling and its associated formation of seed crystals is particularly advantageous. As discussed above, cooling facilitates precipitation. Cooling may even enhance precipitation rate. Seed crystals further facilitate precipitation and may increase the precipitation rate.

As explained above, the metal halide seed crystals form naturally during cooling of the mixture. However, additional metal halide seed crystals may be added to the mixture prior to cooling or during cooling. Adding seed crystals further enhances precipitation and results in larger particles which are easier to separate.

The temperature to which the metal halide/ionic liquid mixture or metal halide/ionic liquid/metal halide seed crystal mixture is cooled can vary. However, the temperature should be lower than the saturation temperature for the particular metal halide to be removed from the ionic liquid. In one embodiment, the mixture can be cooled to a temperature less than about 50° C. In another embodiment, the mixture can be cooled to about room temperature. In yet another embodiment, the mixture can be cooled to a temperature less than about room temperature.

After the precipitated metal halides form, they can be physically separated from the mixture and/or ionic liquid. Any known separation technique can be utilized depending upon time constraints, desired throughput, etc. For example, the precipitated metal halides can be separated by decantation or filtration. Filtration allows for faster separation of the precipitated metal halides, because filtration does not require the precipitated metal halides to settle out of the bulk liquid like decantation. As such, one embodiment of the present process separates the precipitated metal halides from the bulk liquid by filtration.

The process can be either a batch process or a continuous process. Metal halide seed crystals are generally present in a continuous process.

Ionic Liquids

As used herein, the term "ionic liquids" refers to liquids that are composed entirely of ions as a combination of cations and anions. The term "ionic liquids" includes low-temperature ionic liquids, which are generally organic salts with melting points under 100° C. and often even lower than room temperature.

Ionic liquids may be suitable, for example, for use as a catalyst and as a solvent in alkylation and polymerization reactions as well as in dimerization, oligomerization, acetylation, olefin metathesis, and copolymerization reactions. The present embodiments are useful with regard to any ionic liquid catalyst.

One class of ionic liquids is fused salt compositions, which are molten at low temperature and are useful as catalysts, solvents, and electrolytes. Such compositions are mixtures of components, which are liquid at temperatures below the individual melting points of the components.

The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but are not limited to, $BF_4^-$, $PF_6^-$, haloaluminates such as $Al_2Cl_7^-$ and $Al_2Br_7^-$, $[(CF_3SO_2)_2)_2N]^-$, alkyl sulphates ($RSO_3^-$), carboxylates ($RCO_2^-$) and many others. The most catalytically interesting ionic liquids for acid catalysis are those derived from ammonium halides and Lewis acids (such as $AlCl_3$, $TiCl_4$, $SnCl_4$, $FeCl_3$, etc.). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts.

The ionic liquid from which the metal halides are subject to removal can be any ionic liquid. The metal halide removal process as disclosed herein is not limited to regenerated ionic liquid catalysts or ionic liquid catalysts undergoing regeneration. For example, the metal halide removal process may be used to remove metal halide contamination from an ionic liquid.

Process for Regenerating an Ionic Liquid Catalyst

The present process is particularly useful when the ionic liquid is a regenerated ionic liquid catalyst. The present process works most effectively when the ionic liquid catalyst is fully regenerated, meaning that the ionic liquid catalyst is substantially free from conjunct polymers. The presence of conjunct polymers generally increases the solubility of metal halides (e.g. $AlCl_3$) in ionic liquid thereby making it difficult to precipitate out metal halides (e.g. $AlCl_3$). Accordingly, the present process is not nearly as effective when the ionic liquid catalyst is only partially regenerated, meaning that the ionic liquid catalyst still includes conjunct polymers such that it is not substantially free from conjunct polymers.

A used or spent ionic liquid catalyst can be regenerated by contacting the used catalyst with a regeneration metal in the presence or absence of hydrogen. The metal selected for regeneration is based on the composition of the ionic liquid catalyst. The metal should be selected carefully to prevent the contamination of the catalyst with unwanted metal complexes or intermediates that may form and remain in the ionic liquid catalyst phase. The regeneration metal can be selected from Groups III-A, II-B or I-B. For example, the regeneration metal can be B, Al, Ga, In, Tl, Zn, Cd, Cu, Ag, or Au. The regeneration metal may be used in any form, alone, in combination or as alloys.

Regenerating an ionic liquid catalyst in this manner can form excess, dissolved metal halide in the regenerated ionic liquid catalyst. It is then necessary to remove this excess, dissolved metal halide from the regenerated catalyst before it can be recycled to the process utilizing the ionic liquid catalyst and in need of regenerated catalyst. Moreover, the metal halide must be removed to prevent it from accumulating in the regeneration zone and other parts of the regeneration unit and causing plugging problems.

For example, deactivated, or at least partially deactivated, chloroaluminate ionic liquid catalyst can be reacted with aluminum metal, in the presence or absence of hydrogen, to regenerate the chloroaluminate ionic liquid catalyst. However, the reaction with aluminum metal can form excess, dissolved $AlCl_3$ in the regenerated chloroaluminate ionic liquid catalyst. It is necessary to remove this excess, dissolved $AlCl_3$ prior to recycling the regenerated chloroaluminate ionic liquid catalyst to, for example, an alkylation reaction.

Accordingly, the present disclosure further provides a process for regenerating an ionic liquid catalyst. Such regeneration process includes the following steps: a) reacting an ionic liquid catalyst with aluminum to provide a regenerated ionic liquid catalyst containing excess $AlCl_3$; b) precipitating the excess $AlCl_3$ from the regenerated ionic liquid catalyst to provide precipitated excess $AlCl_3$; and c) removing the precipitated excess $AlCl_3$ from the regenerated ionic liquid catalyst.

As used herein, the term "excess $AlCl_3$" refers to the amount of $AlCl_3$ produced during catalyst regeneration that is beyond its solubility limit in the ionic liquid catalyst at a particular temperature such that it may precipitate out during the regeneration process.

As described above, the precipitating step can be accomplished through cooling. More specifically, the precipitating step can involve cooling the regenerated ionic liquid catalyst to precipitate excess $AlCl_3$ from the regenerated ionic liquid catalyst. This cooling step generally provides $AlCl_3$ seed crystals, which are the building blocks for larger particles of precipitated excess $AlCl_3$ as described above. After the precipitated excess $AlCl_3$ forms, it can be separated from the mixture and/or ionic liquid. The temperatures and separation techniques discussed above with regard to metal halides in general also apply to $AlCl_3$.

Process for Removing Metal Halides from an Ionic Liquid in a Crystallization Vessel Yet another embodiment of the process involves removing metal halides from an ionic liquid in a crystallization vessel. This embodiment can be better understood with reference to FIG. 1, which schematically illustrates this embodiment.

As shown in FIG. 1, the process includes feeding the ionic liquid comprising metal halides 1 to a vessel 10 and providing metal halide seed crystals to provide a mixture 9 comprising ionic liquid, metal halides, and metal halide seed crystals. The process further includes cooling the mixture 9 in the vessel 10 to provide precipitated metal halides and removing the precipitated metal halides from the vessel 10. Larger precipitated metal halides will eventually settle to the bottom portion 11 of the vessel 10 where they can exit the vessel 10, for example, in an effluent stream 2 comprising such precipitated metal halides.

The metal halide seed crystals can be provided by cooling, outside addition of metal halide seed crystals, or a combination thereof. The source of the metal halide seed crystals can depend upon whether the process is batch or continuous.

The cooling can be achieved by internally cooling the vessel contents (e.g. by a cooling jacket), externally cooling the vessel contents (e.g. by an external cooling loop), or a combination of both internally and externally cooling the vessel contents.

The vessel 10 can be constructed such that it allows for removal of a least a portion of the mixture, from an upper portion 12 of the vessel 10; cooling the portion in a heat exchanger 4; and reintroducing the portion into the vessel 10. In FIG. 1, the portion that is removed from the mixture 9 is labeled as stream 3 and the cooled portion that is reintroduced into the vessel 10 is labeled as stream 7. Such an external cooling loop 20 can provide certain advantages. Removing mixture from the upper portion 12 of the vessel 10 ensures a large amount of rather small metal halide particles, rather than large metal halide particles, enter the external cooling loop 20. Additional metal halide precipitation occurs upon cooling of the removed portion. The small metal halide particles act as seed crystals such that metal halide dissolved in the ionic liquid precipitates onto these particles thereby providing larger precipitated particles. Dissolved metal halide precipitates onto these small metal halide particles rather than the heat exchanger walls. Furthermore, the reintroduction of the portion can agitate the mixture in the vessel and prevent seed crystals from adhering the walls of the vessel.

The removed portion 3 can be filtered prior to cooling the removed portion. In FIG. 1, such a filtering step occurs in a filter 5. Filtering the removed portion 3 prevents any large metal halide particles from entering the external cooling loop 20. The removed portion 3 subjected to filtration provides a filtered, removed portion 6, which can then be cooled in the heat exchanger 4 to provide the cooled, removed portion 7, which is reintroduced to the vessel 10.

The reintroduction or recycle rate of the cooled, removed portion 7 into the vessel 10 should be significant. For example, the cooled, removed portion 7 can be reintroduced into the vessel 10 at a rate between about 5 and about 50 times the feed rate of the ionic liquid. In one embodiment, the cooled, removed portion 7 can be reintroduced into the vessel 10 at a rate between about 10 and about 20 times the feed rate of the ionic liquid. Such a significant recycle rate is beneficial because it provides a high heat transfer coefficient, reduces the required temperature change of the removed portion in the heat exchanger, and sweeps precipitate from the heat exchanger walls thereby reducing coating of the heat exchanger walls.

Over time, the walls of the heat exchanger could become coated with precipitated solid and will need to be cleaned. Therefore, it is desirable to use a duplicate spare heat exchanger in the process for removing metal halides from an ionic liquid. When coating of precipitate on the heat exchanger walls reduces heat transfer below a lower acceptable limit, flow of the removed portion to the heat exchanger can be stopped and switched to the duplicate spare heat exchanger. Then the first heat exchanger can be cleaned. After cleaning, flow of the removed portion to the duplicate spare heat exchanger can be stopped and resumed in the first heat exchanger. In this manner, the process can run without interruption.

To prevent deposition of precipitate on heat exchanger walls, they can be treated to reduce nucleating sites. For example, the heat exchanger walls can be polished or coated with a smooth material.

The feed of ionic liquid containing metal halides may also be pre-cooled before it enters the crystallization vessel. Pre-cooling the feed can be accomplished by pre-mixing it with the cooled, removed portion or bringing the feed and the cooled, removed portion into close contact.

The vessel can be jacketed for cooling and/or heating. A cooling and/or heating jacket, shown in FIG. 1 as item 8, is useful to provide additional cooling, adjust for any heat transfer to or from the surroundings, maintain the vessel walls slightly warmer than its contents to prevent precipitation on the vessel walls, and remove precipitate from the vessel walls during cleaning.

The mixture 9 can be agitated by any known agitation method provided that the agitation method does not destroy the metal halide seed particles present in the mixture 9. For example, as shown in FIG. 1, an impeller 13 can agitate the mixture 9. Flow of the mixture 9 within the vessel 10 can also be regulated by any known flow regulation method. For example, as shown in FIG. 1, baffles 14 can regulate flow of the mixture 9.

Alkylation Process

Another embodiment as described herein relates to an alkylation process, which utilizes the above-described metal halide (e.g. $AlCl_3$) precipitation process. The alkylation process first involves conducting an alkylation reaction with an ionic liquid catalyst to provide a product and a spent ionic liquid catalyst. The spent ionic liquid catalyst is then reacted with aluminum to provide a regenerated ionic liquid catalyst and excess $AlCl_3$. The excess $AlCl_3$ is precipitated from the regenerated ionic liquid catalyst to provide precipitated excess $AlCl_3$, which is removed from the regenerated ionic liquid catalyst. The regenerated ionic liquid catalyst is recycled to the alkylation reaction.

The following examples are provided to further illustrate the present process and the advantages thereof. The examples are meant to be only illustrative, and not limiting.

EXAMPLES

Example 1

Precipitation of $AlCl_3$ from Regenerated Ionic Liquid Catalyst

A 300 cc autoclave was charged with 50.60 gm spent ionic liquid catalyst (n-butyl pyridinium chloroaluminate) containing 24.3 wt % conjunct polymers (acid soluble oils), 65 gm anhydrous normal hexane and 8 gm aluminum powder. The autoclave was sealed and heated to 100° C. for 90 minutes to reactivate the catalyst. At the end of the heating period, the autoclave and its contents were cooled to room temperature. The top organic layer (immiscible in the ionic liquid phase), containing the liberated conjunct polymers, was separated from the ionic liquid by decantation. The ionic liquid phase was rinsed with additional hexane (2×50 ml) to ensure the removal of all liberated conjunct polymers. The organic rinses were combined and concentrated under a pressure on a rotary evaporator to give 10.5 gm of conjunct polymers as reddish viscous oil. The ionic liquid layer (regenerated ionic liquid catalyst) was filtered in a glove box (oxygen and moisture free environment) to separate the catalyst from excess aluminum powder. The regenerated catalyst was obtained in 33 gm as clear amber liquid. A small aliquot (10 gm) of the regenerated ionic liquid was hydrolyzed with excess water and then extracted with hexane. The hexane layer was dried over anhydrous magnesium sulfate ($MgSO_4$), filtered and concentrated to retrieve any residual conjunct polymers that may have remained in the catalyst. Only 0.07 gm conjunct polymers remained in the test sample. The remainder of the regenerated catalyst was transferred to a vial and kept in the glove box at room temperature. A few hours later, the catalyst was checked and a fine off-white powder (aluminum trichloride) had settled at the bottom of the vial. The same observation was seen in several regeneration experiments.

Example 2

Recrystallization of Added $AlCl_3$ from Fresh Ionic Liquid Catalyst

To 20 gm of freshly-made ionic liquid catalyst (n-butyl-pyridinium chloroaluminate) with an Al/N ratio of 2, 6.7 wt % $AlCl_3$ was added and dissolved by heating the catalyst to 100° C. The mixture was allowed to cool gradually to room temperature. The added $AlCl_3$ started to crash out of the catalyst soon after the cooling started and completely precipitated out within 2.5 hours.

Example 3

Recrystallization of Added $AlCl_3$ from Fully Regenerated Catalyst

To 20 gm of fully regenerated n-butyl-pyridinium chloroaluminate ionic liquid catalyst containing <0.2 wt % conjunct polymers, 6.7 wt % $AlCl_3$ was added and dissolved by heating the catalyst to 100° C. The mixture was allowed to cool off gradually at room temperature. The added $AlCl_3$ started to crash out of the catalyst soon after the cooling started and completely precipitated out within 4 hours. Accordingly, the precipitation of added aluminum trichloride from the fully regenerated catalyst seems to behave similarly to the freshly-made catalyst.

Example 4

Recrystallization of Added $AlCl_3$ from Partially Regenerated Catalyst

To 30 gm of partially regenerated n-butyl-pyridinium chloroaluminate ionic liquid catalyst containing ~2 wt % conjunct polymers, 9.8 wt % $AlCl_3$ was added and dissolved by heating the catalyst to 100° C. The mixture was allowed to cool off gradually at room temperature. The added $AlCl_3$ started to precipitate out of the catalyst very slowly. It took several hours to visibly see $AlCl_3$ precipitation at the bottom of the vial. It took nearly 72 hrs for ~75% of the added $AlCl_3$ to precipitate out as determined by filtering the precipitated solids out.

In comparison to Example 3, Example 4 shows that the process for removing metal halides from an ionic liquid as described herein is not as useful and efficient with partially regenerated ionic liquid catalyst. Rather, the process is more useful and efficient with fully regenerated ionic liquid catalyst.

Example 5

Continuous Crystallization of AlCl$_3$ from Regenerated Ionic Liquid Catalyst Crystallization of AlCl$_3$ from regenerated catalyst was performed in a continuous crystallization unit. An ionic liquid solution containing 0.1 wt % conjunct polymers (CP) and 6 wt % of AlCl$_3$ was prepared prior to the experiment by adding 33.2 g of AlCl$_3$ powder with 99.999% purity into 350 ml of regenerated ionic liquid catalyst. The prepared ionic liquid solution was then charged into the continuous crystallization unit, which consisted of a 200 ml ChemGlass crystallizer equipped with a 1.5 inch diameter overhead stirrer and heating/cooling jacket, a tubing pump, and a 250 ml flask as catalyst reservoir above a heating mantle. Tubes connecting these items were wrapped with heating tape. A Lasentec® FBRM probe manufactured by Mettler-Toledo was used for particle size distribution measurement.

The crystallization experiments were conducted at 4° C. and atmospheric pressure with overhead stirring at 400 RPM. From the bottom of the crystallizer, a small stream of the slurry containing AlCl$_3$ crystals and ionic liquid solution was continuously withdrawn and pumped by the tubing pump to the catalyst reservoir. AlCl$_3$ crystals in this stream were dissolved back into the ionic liquid solution by heating the tubes and the catalyst reservoir to 180° F., which was well above the temperature needed to dissolve 6 wt % AlCl$_3$ in ionic liquid. This ionic liquid solution which was free of AlCl$_3$ crystals was fed back to the crystallizer as feed. The recirculation flow rate was carefully controlled by the pump and resulted in a residence time of 6 hours in the crystallizer.

Figure 2:
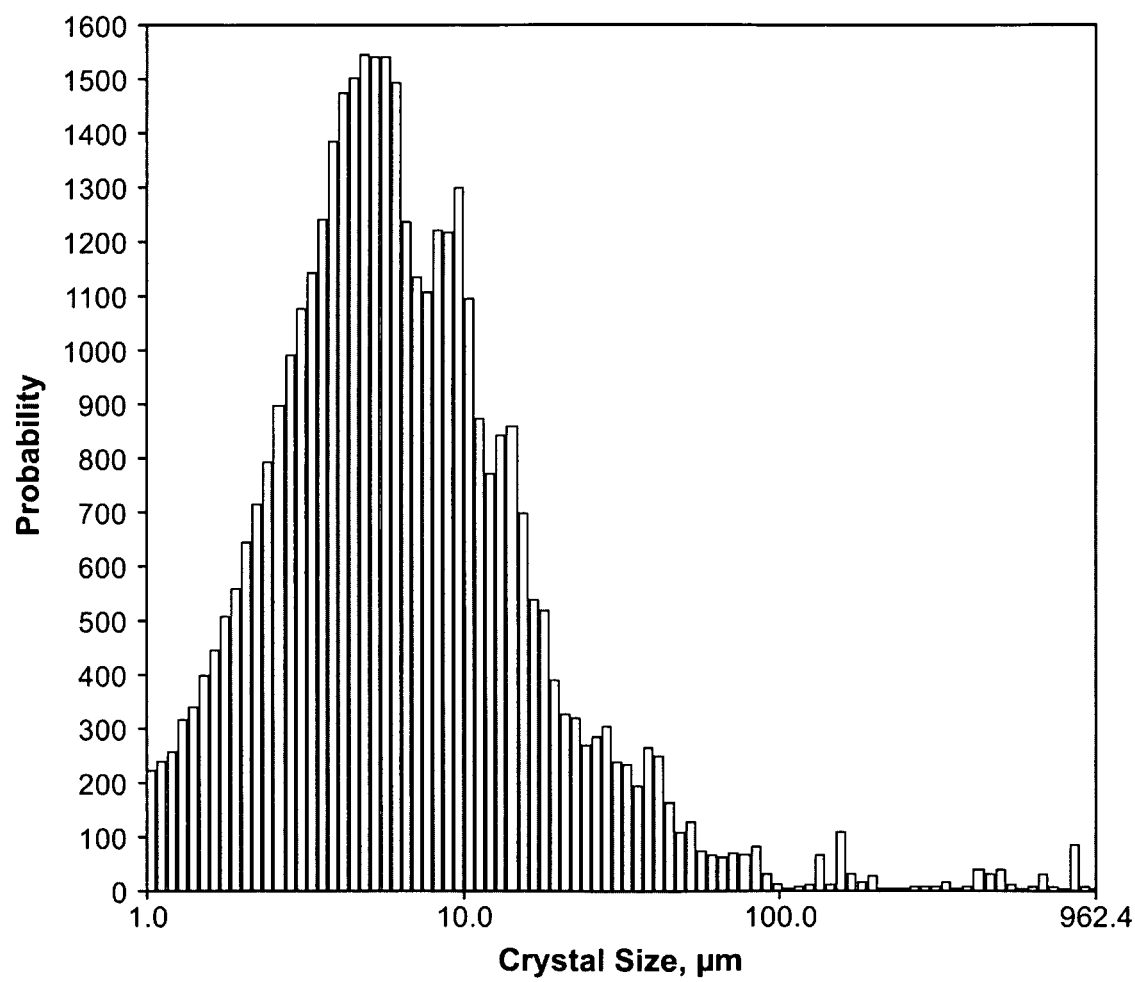
FIG. 2 depicts particle size distribution of $AlCl_3$ crystals precipitated in Example 5.

The particle size distribution of the AlCl$_3$ crystals was monitored and recorded continuously by the FBRM probe. FIG. 2 shows the particle size distribution measured by the FBRM probe when the system reached a steady state.

Although the present processes have been described in connection with specific embodiments thereof, it will be appreciated by those skilled in the art that additions, deletions, modifications, and substitutions not specifically described may be made without departing from the spirit and scope of the processes as defined in the appended claims.

That which is claimed is:

1. A process for removing dissolved metal halides from an ionic liquid, comprising:
    a) feeding the ionic liquid comprising dissolved metal halides to a vessel and providing metal halide seed crystals to provide a mixture comprising ionic liquid, dissolved metal halides, and metal halide seed crystals;
    b) cooling the mixture in the vessel to provide precipitated metal halides;
    c) removing the precipitated metal halides from the vessel, and
    d) removing from an upper portion of the vessel at least a portion of the mixture, cooling the portion in a heat exchanger, and reintroducing the portion to the vessel.

2. The process according to claim 1, further comprising filtering the removed portion prior to cooling the removed portion.

3. The process according to claim 2, wherein the removed portion is reintroduced into the vessel at a rate between 5 and 50 times an ionic liquid feed rate.

4. The process according to claim 1, further comprising separating the precipitated metal halides from the mixture by decantation or filtration.

5. The process according to claim 1, further comprising separating the precipitated metal halides from the mixture by filtration.

6. The process according to claim 1, wherein the mixture is cooled to a temperature less than 50° C.

7. The process according to claim 1, wherein the mixture is cooled to room temperature or to less than room temperature.

8. The process according to claim 1, wherein the ionic liquid is a regenerated ionic liquid catalyst.

9. The process according to claim 1, wherein the metal halide is AlCl$_3$.

10. The process according to claim 1, wherein the metal is a Group III-A, II-B, or I-B metal.

* * * * *